(12) United States Patent
Lee (10) Patent No.: US 10,967,029 B2
(45) Date of Patent: Apr. 6, 2021

(54) **METHOD OF USING *CISTANCHE TUBULOSA* EXTRACT TO PREVENT, SLOW DOWN, OR TREAT AN EYE DISEASE CAUSED BY OXIDATIVE STRESS**

(71) Applicant: Sinphar Pharmaceutical Co., Ltd., Taipei (TW)

(72) Inventor: Chih-Wen Lee, Yilan County (TW)

(73) Assignee: Sinphar Pharmaceutical Co., Ltd., Taipei (TW)

( * ) Notice: Subject to any disclaimer, the term of this patent is extended or adjusted under 35 U.S.C. 154(b) by 291 days.

(21) Appl. No.: 15/854,722

(22) Filed: Dec. 26, 2017

(65) Prior Publication Data

US 2018/0117109 A1 May 3, 2018

Related U.S. Application Data

(63) Continuation of application No. 14/790,017, filed on Jul. 2, 2015, now abandoned.

(60) Provisional application No. 62/020,409, filed on Jul. 3, 2014.

(51) Int. Cl.
| | | |
|---|---|---|
| *A61K 36/64* | (2006.01) | |
| *A23L 5/00* | (2016.01) | |
| *A23L 33/105* | (2016.01) | |

(52) U.S. Cl.
CPC ........... *A61K 36/64* (2013.01); *A23L 5/00* (2016.08); *A23L 33/105* (2016.08)

(58) Field of Classification Search
None
See application file for complete search history.

(56) References Cited

U.S. PATENT DOCUMENTS

| | | | |
|---|---|---|---|
| 9,339,522 B2 | 5/2016 | Kong et al. | |
| 2009/0301508 A1 | 12/2009 | Wang et al. | |
| 2012/0009131 A1* | 1/2012 | Lin | A61K 8/602 424/48 |
| 2014/0357581 A1 | 12/2014 | Kong et al. | |

FOREIGN PATENT DOCUMENTS

| | | |
|---|---|---|
| CN | 1526400 A | 9/2004 |
| CN | 101331906 A | 12/2008 |
| CN | 102813753 A | 12/2012 |
| CN | 103156867 A | 6/2013 |
| CN | 103896997 A | 7/2014 |
| EP | 2792361 A1 | 10/2014 |
| JP | 2007191416 A | 8/2007 |
| JP | 2008297283 A | 12/2008 |
| JP | 2013023487 A | 2/2013 |
| JP | 2014084319 A | 5/2014 |
| WO | 0134169 A1 | 5/2001 |
| WO | 2008116391 A1 | 10/2008 |
| WO | 2009146594 A1 | 12/2009 |
| WO | 2012158591 A1 | 11/2012 |
| WO | 2013087042 A1 | 6/2013 |

OTHER PUBLICATIONS

Barnstable (2009) j ocul biol dis inform 2:145-148. (Year: 2009).*
Chiras et al. (2015) Crit. Rev. Clin. Lab. Sci. 52:1, 12-27. (Year: 2015).*
Guo et al. (2013) Amer. J. Alzheimer's Disease and other Dementias 28(4): 363-370. (Year: 2013).*
Izuta et al. (2010) Molecular Vision 16: 130-136. (Year: 2010).*
Li et al. (2016) Front. Pharmacol. vol. 7, Article 41, 7 pages (Year: 2016).*
Liao et al. (2018) Food and Chemical Toxicology 118: 581-588. (Year: 2018).*
Raskin et al. (2004) Current Pharmaceutical Design, 10, 3419-3429. (Year: 2004).*
Revilla et al. (1998) J. Agric. Food Chem. 46, 4592-4597. (Year: 1998).*
Wielgus et al. (2010) Photochem, Photobiol. Sci. 9, 1505-1512. (Year: 2010).*
Wu et al. (2018) Cell Physiol Biochem 51: 63-79. (Year: 2018).*
Liu Shi-qiao et al., "Research advance on medicinal plants of Clerodendrum", Drug Evaluation Research, vol. 34, No. 6, pp. 469-473, Dec. 2011.
Shi Yongfeng, "Common Eye Diseases From 0 to 100 Years Old", Zhengzhou University Press, p. 82, 1st edition, Sep. 2013.
Li Qiang et al., "New Edition of Manual of Common Active Ingredients in Chinese Traditional Medicine", China Union Medical University Press, pp. 159 and 365, 1st edition, Jan. 2008.
Hui Yongzheng, "Natural Products of Traditional Chinese Medicine 3 Medium Natural Products", Shanghai Science and Technology Press, p. 1884, Jan. 2011.
Wang Zhentao et al., "Monograph for Quality Evaluation of Chinese Herbal Medicine", Shanghai Science and Technology Press, p. 326, Jan. 2013.
Database WPI Week 201446 Thomson Scientific, London, GB; AN 2014-J31623 XP002779634 & JP2014084319A, May 12, 2014.
Lori Ventura, "Introduction: complementary medicine in ophthalmology", Journal of Ocular Biology, Diseases, and Informatics, 2009, p. 95-p. 97.
Natalia A. Stefanova et al., "Effects of Cistanche deserticola on behavior and signs of cataract and retinopathy in senescence-accelerated OXYS rats", Journal of Ethnopharmacology, Oct. 10, 2011, p. 624-p. 632, vol. 138.
Yong Jiang et al., "Analysis of chemical constituents in *Cistanche* species", Journal of Chromatography A, 2009, p. 1970-1979, vol. 1216.
Wang et al., "Protective effect on rat retinal ganglion cells and the safety of intravitreal injected acteoside", Chinese Journal of Ocular Fundus Diseases., vol. 29, No. 6, Nov. 2013, pp. 593-599.

(Continued)

*Primary Examiner* — Russell G Fiebig
(74) *Attorney, Agent, or Firm* — CKC & Partners Co., LLC (57) ABSTRACT

This invention provides a method of using extract of *Cistanche tubulosa*. The extract was used to prevent, slow down, or treat an eye disease caused by oxidative stress. The method includes administrating to a subject in need a therapeutically effective amount of the extract of *Cistanche tubulosa* to prevent, slow down, or treat an eye disease caused by oxidative stress.

4 Claims, 13 Drawing Sheets

(56) References Cited

OTHER PUBLICATIONS

Hiroshi Kohda et al., "Studies on Lens-Aldose-Reductase Inhibitor in Medicinal Plants. II. Active Constituents of Monochasma savatierii FRANCH. et MAXIM.", Chem. Pharm. Bull., vol. 37, No. 11, Nov. 1989, pp. 3153-3154.

Bruce E.Onofrey et al., Ocular Therapeutics Handbook: A Clinical Manual, Third Edition, pp. 530-533, Aug. 2013 (First Edition).

Peng Qinghua et al., Chinese and Western Medicine Clinical Medicine Manual, Volume Ophthalmology, Hunan Science and Technology Publisher, p. 264, The First Printing of the First Edition in Mar. 2010.

Bruce E.Onofrey et al., Ocular Therapeutics Handbook: A Clinical Manual, Third Edition, pp. 568-571, Aug. 2013 (First Edition).

Yang Xinguang et al., Modern Ophthalmic Drug Therapy, People's Military Medical Publisher, p. 271, First Edition, Sep. 2000.

Sheng Yan-Juan et al., "Therapeutic Development of Age Related Macular Degeneration", Journal of clinical ophthalmology, 2004, 471-474, vol. 12, No. 5.

M. Mosca et al., "Ocular tissues and fluids oxidative stress in hares fed on verbascoside supplement", International Journal of Food Sciences and Nutrition, Mar. 31, 2014, p. 235-p. 240, 65(2), ISSN: 0963-7486.

Chen Fei et al., "Research process in Cistanche Herba", Drug Evaluation Research, Dec. 2013, 469-473, vol. 36, No. 6.

Zhang Ai-xiang et al., "Study on the anti-oxidation effect of echinacoside", Practical Geriatrics, Aug. 2009, 310-312, vol. 23, No. 4.

B. Blazics et al., "Identification and LC-MS-MS Determination of Acteoside, the Main Antioxidant Compound of Euphrasia Rostkoviana, Using the Isolated Target Analyte as External Standard", Journal of Chromatographic Science, Mar. 2011, 203-207, vol. 49.

Barnstable (2009) J. Ocul. Biol. 2 : 145-148.

Seok et al. (2015) Clin. Nutr. Res. 4 : 124-131.

Shimoda et al. (2009) The Amer. J. Chinese Med. vol. 37, No. 6, 1125-1138.

Xiong et al. (2013) J. Ethnopharmacol. 150 : 935-945.

\* cited by examiner

METHOD OF USING *CISTANCHE TUBULOSA* EXTRACT TO PREVENT, SLOW DOWN, OR TREAT AN EYE DISEASE CAUSED BY OXIDATIVE STRESS

RELATED APPLICATIONS

This application is a continuation of U.S. application Ser. No. 14/790,017, filed Jul. 2, 2015, which claims priority to U.S. provisional application Ser. No. 62/020,409, filed Jul. 3, 2014, all of which are herein incorporated by reference.

BACKGROUND

Technical Field

This invention relates to a use of *Cistanche tubulosa*'s extract, especially relating to a use of preparing drugs or food for protecting eye cells.

Description of Related Art

The eyes are the windows of the soul. The world can be seen through the eyes in an ultra-high resolution. Everyday life has to rely on the eyes. Current common eye diseases include age-related macular degeneration (AMD), diabetic retinopathy, and proliferative vitreoretinopathy (PVR), wherein the AMD is considered to be a critical eye disease to cause blindness in adults or elderly.

According to the World Health Organization (WHO), AMD, suppressing cataract, has become the most common cause to poor vision (Jager et al 2008). In the report of 2010, the number of vision diminution and blindness caused by AMD is increased. According to the US national statistics, over 8 million people suffer from AMD, wherein more than 10% of people in the age between 65 and 74 suffer from AMD, and more than 10% of people over 74 suffer from AMD. It is estimated that over 50% of the population will suffer AMD in 2020 (Friedman et al 2004). The prevalence of AMD of elderly more than 65 years is about 10% in Taiwan, and the prevalence of AMD is lower than Europe and America. However, people have limited cognition to the macular degeneration, and there is no effective treatment to AMD. Therefore, when the patients are diagnosed with AMD, the doctors cannot give effective treatments. Hence, macular degeneration has become the main cause of blindness in people and is called "the number one killer of vision". Therefore, prevention is especially important for AMD. Moreover, Taiwanese population is aging, and the lifestyle is gradually westernized. AMD will be widespread and become the major eye diseases in adults, when other causes of blindness are under controlled.

Free radical will accumulate oxidative stress damages on DNA, proteins, lipids, and intercellular macromolecular materials and cause aging. In addition to the central nervous system degeneration, some eye diseases (especially macular degeneration and retinopathy) are also considered to be highly related to oxidative stress damages.

However, there are no methods to effectively prevent, slow down, or treat eye diseases or protecting eye cells. This is a problem to be solved.

SUMMARY

This invention provides a method of using extract of *Cistanche tubulosa* for preparing drugs or food for protecting eye cells.

According to an embodiment, the extract of *Cistanche tubulosa* comprises echinacoside, acteoside, isoacteoside, tubuloside A, or a combination thereof.

According to another embodiment, the drugs or food are used to prevent, slow down, or treat eye diseases.

According to yet another embodiment, the eye diseases are macular degeneration, macular hole, retinopathy, or glaucoma.

According to yet another embodiment, the macular degeneration is age-related macular degeneration.

According to yet another embodiment, the age-related macular degeneration is dry macular degeneration or wet macular degeneration.

According to yet another embodiment, the retinopathy is diabetic retinopathy, retinitis pigmentosa, retina disease, retinal artery and vein occlusion, proliferative vitreoretinopathy, or central serous retinopathy.

According to yet another embodiment, a form of the drugs is capsule, tablet, powder, or liquid.

The extract of *Cistanche tubulosa* of the instant disclosure is used to prepare drugs or food having a function of protecting eye cells.

BRIEF DESCRIPTION OF THE DRAWINGS

For the features, advantages and embodiments of the instant disclosure to become more apparent, the accompanying drawings are described below.

DETAILED DESCRIPTION

In order to make the description of this disclosure more detailed and complete, the embodiments of the instant disclosure are illustratively described below. However, this is not the only form of practicing or using the embodiments of the instant disclosure. The disclosed various embodiments may be combined or substituted by each other and one embodiment may be added with other embodiments in a beneficial situation. In the following description, numerous specific details will be described in detail in order to enable the reader to fully understand the following embodiments. However, embodiments of the instant disclosure may be practiced without certain specific details.

This invention provides a method of using extract of *Cistanche tubulosa* for preparing drugs or food to protect eye cells.

*Cistanche tubulosa* is also called "desert ginseng" and is a type of *Cistanche*. Traditionally, *Cistanche tubulosa* is a drug used to invigorates the kidney and as an aphrodisiac. It can be used to treat impotence, infertility, weakness, sore waist and knee, and constipation. *Cistanche tubulosa* has been an entry in "Chinese Pharmacopoeia" since the 2005 edition. *Cistanche* has effects of anti-oxidation, protecting nerve cell (such as inhibiting neuronal apoptosis), promoting nerve growth factor secretion, regulating brain neurotransmitters, improving learning and memory, and reducing the generation of brain amyloid.

According to an embodiment, the extract of *Cistanche tubulosa* comprises echinacoside, acteoside, isoacteoside, tubuloside A, or a combination thereof. All of the echinacoside, acteoside, isoacteoside, and tubuloside A have a protecting effect to the eye cells.

In the instant disclosure, the method of preparing drugs or food for protecting eye cells from the extract of *Cistanche tubulosa* comprises providing extract of *Cistanche tubulosa* and preparing drugs or food for protecting eye cells from the extract of *Cistanche tubulosa*. For example, the method of preparing drugs or food for protecting eye cells from the extract of *Cistanche tubulosa* comprises extracting the extract from *Cistanche tubulosa*. Next, the extracted components of *Cistanche tubulosa* is added with excipients and processed to form drugs or food. Alternatively, the extracted components of *Cistanche tubulosa* may be directly obtained and then added with excipients and processed to directly form drugs or food.

It is noteworthy that the drugs and food prepared from extract of *Cistanche tubulosa* may comprise at least one of the four components described above, and optionally comprise other common excipients used in drugs or food. Moreover, the drugs and food prepared from extract of *Cistanche tubulosa* may be in any forms, such as capsules, tablets, powder, or liquid.

According to an embodiment of the instant disclosure, the drugs or food are used to prevent, slow down, or treat eye diseases.

According to another embodiment, the eye diseases are macular degeneration, macular hole, retinopathy, or glaucoma.

According to yet another embodiment, the macular degeneration is age-related macular degeneration. According to the clinical and pathological expressions, the age-related macular degeneration may be divided into dry macular degeneration and wet macular degeneration.

According to yet another embodiment, the retinopathy is diabetic retinopathy, retinitis pigmentosa, retina disease, retinal artery and vein occlusion, proliferative vitreoretinopathy, or central serous retinopathy.

According to the instant disclosure, the extract of *Cistanche tubulosa* is used to prepare food or drugs, wherein the components of the extract of *Cistanche tubulosa* comprise echinacoside, acteoside, isoacteoside, tubuloside A, or a combination thereof. These components can decrease the damage of the oxidative stress to the eye cells, and thus make the prepared drugs or food have protecting effects to the eye cells. The extract of *Cistanche tubulosa* may be further developed to drugs for slowing down the progress of eye diseases and especially may be used to treat the retinopathy diseases.

Several embodiments are listed below to elaborate the method of the instant disclosure. However, these embodiments are intended as examples and not used to limit the instant disclosure. Therefore, the scope of the invention should be as defined by the appended claims.

Embodiment 1

Embodiment 1 of the instant disclosure is to prepare extract of *Cistanche tubulosa*. The method comprises the following steps.

1. 10 kg of *Cistanche tubulosa*'s succulent stem was taken and sliced. Then, the sliced succulent stem was immersed in water 8 times the volume of the stem for 1 hour and cooked for 2 hours. After filtering, the filtrate was collected.
2. The filtered residue was added with water 6 times of the volume of the residue and cooked twice, each time for 1 hour. The filtrate was collected.
3. Filtrate from the three cooking was combined and concentrated under a reduced pressure at 50° C. until the weight ratio was 1.10. Ethanol was added until the concentration was 60%. After being refrigerated for 12 hours, the supernatant was poured out and then concentrated under a reduced pressure at 50° C. and ethanol was recycled until the weight ratio was 1.10. 6 kg of crude extracts was obtained.
4. Water of one time volume to the crude extract from step 3 was added and heated to dissolve the crude extract in step 3. Next, water 4 times the volume and 40% EtOH 5 times the volume were used to perform elution. Next, the aqueous eluent was infused into a column filled with a macroporous resin. The column was eluted by water 3 times the volume, and the water eluent was discarded. Afterwards, the column was eluted by 40% EtOH 4 times the volume.
5. Two 40% EtOH eluent in step 4 was collected and then concentrated and dried to obtain 1107 g extract of *Cistanche tubulosa*. The extract of *Cistanche tubulosa* comprises echinacoside, acteoside, isoacteoside, and tubuloside A.

Embodiment 2-5

In the instant disclosure, echinacoside was used in embodiment 2. Acteoside was used in embodiment 3. Isoacteoside was used in embodiment 4. The above materials were all purchased from ChromaDex, USA. Tubuloside A (purchased from Tauto Biotech, Shanghai, China) was used in embodiment 5.

Cell Culture

Retinal pigment epithelial (RPE) was located between the retinal neuroepithelial layer and the choroid. RPE is in charge of many physiological functions, such as retinal barrier, phagocytosis, participating the visual cycle and metabolism, antioxidant function, and secreting growth factors, etc. RPE cells are susceptible to oxidative stress damages and then cell death causing retinopathy, visual dysfunction, and even loss of visual function. Therefore, RPE cells are usually used to study the cell model of eye-related diseases.

In a case of age-related macular degeneration, since the age-related macular degeneration is closely related to the oxidative stress of vascular endothelial growth factor (VEGF), deposition of lipofuscin (Delori F C et al, 2001), chronic inflammation, and mutation of complement system, RPE cells are used in the study. In age-related macular degeneration, the oxidative stress will cause damage of RPE cells or choriocapillaris (Boltz A et al, 2010). The damage of RPE cells will cause inflammation of Bruch membrane, and the dysfunction of the RPE cells and the triggered inflammation will cause abnormal deposition of extra cellular matrix (ECM) to affect the biological function of RPE cells and deteriorate the progress of age-related macular degeneration.

RPE cells (purchased from American Type Culture Collection, abbreviated as ATCC) are used in the embodiments below to evaluate the protective effects to the eye cells in embodiments 1-5 of the instant disclosure. The cell culturing comprises the following steps.

1. RPE cell clones were taken out from anti-frozen tubes in liquid nitrogen and quickly moved to a sterile hood after thawed in 37° C. water bath for 1 minute. RPE cell clones were taken out and placed in 10 cm dishes having 10 mL DMEM (Dulbecco's Modified Eagle Medium) therein. 10% inactivated fetal bovine serum (FBS), 2 mM L-glutamine, 100 U/mL penicillin, and 100 g/mL streptomycin were added into the DMEM.
2. The dishes were placed in a 37° C. incubator and cultured in conditions of a mixture gas of 95% air and 5% $CO_2$, as well as 70% humidity. The old mediums were replaced by fresh mediums every 3 days. Serum-free DMEM was used instead of the mediums before performing experiments.
3. When cells proliferated to nearly saturation, the numbers of cells were counted by a cell counter. When the cell numbers reached about $2 \times 10^5$-$1 \times 10^6$ cells/mL, the cells were diluted in a ratio of 1:3 to perform subculture. Since RPE cells are attachment type cells, the medium containing the cells was transferred into 15 mL centrifugation tubes and then centrifuged at 72 g for 5 mines at room temperature when the medium was replaced. After centrifugation, the supernatant was removed and then fresh medium was added for culturing.

The examples below were used to evaluate the effects of the embodiments 1-5 of the instant disclosure by using the cultured RPE cells.

Example 1: Cell Viability and Growth Measurement of RPE Cells (MTT Assay)

Before experiments, the medium was replaced by serum-free medium. Fixed quantity of RPE cells ($2 \times 10^5$ cells/mL) were respectively placed in a 96-well plate. After placed in an incubator, the cells were cultured for 24 hours after treated by various concentrations of embodiments 1-5. Next, 1.0 mg/mL 3-(4,5-Dimethylthiazol-2-yl)-2,5-diphenyltetrazolium bromide (MTT) was added and reacted at 37° C. for 1 hour. Afterwards, 200 µL dimethyl sulfoxide (DMSO) was added into each well and shake in the dark at room temperature for 10 minutes after slight mixing. After the residual cells were completely dissolved, an enzyme immunoassay analyzer (MRX microplate reader, USA) was used to detect the 550 nm absorbance of each well. The cells untreated by embodiments were used as a control group after culturing for 24 hours.

One purpose of the example 1 is to test the cytotoxicity of the embodiments 1-5 to the RPE cells and the promotion of the embodiments 1-5 to the RPE cell growth. The mitochondrial enzyme of live cells can reduce the MTT to formazan of purple crystal dissolved by DMSO. In short, the metabolic activity of cells is used to determine whether cells are alive or not. The measured dissolving absorbance is equal to the cell viability. Therefore, the more the cells alive, the higher the absorbance. The calculating formula of the cell viability was shown below.

Cell viability (%)=(light absorbance after cells treated by drugs for 24 hours/light absorbance of the control group after 24 hours)×100%

The results of the example 1 was expressed by the mean standard error of the number of experiments (mean±S.E.). The statistical analysis was performed by Student's t-test or one way ANOVA. If P<0.05, it indicates a significant difference.

Figure 1:
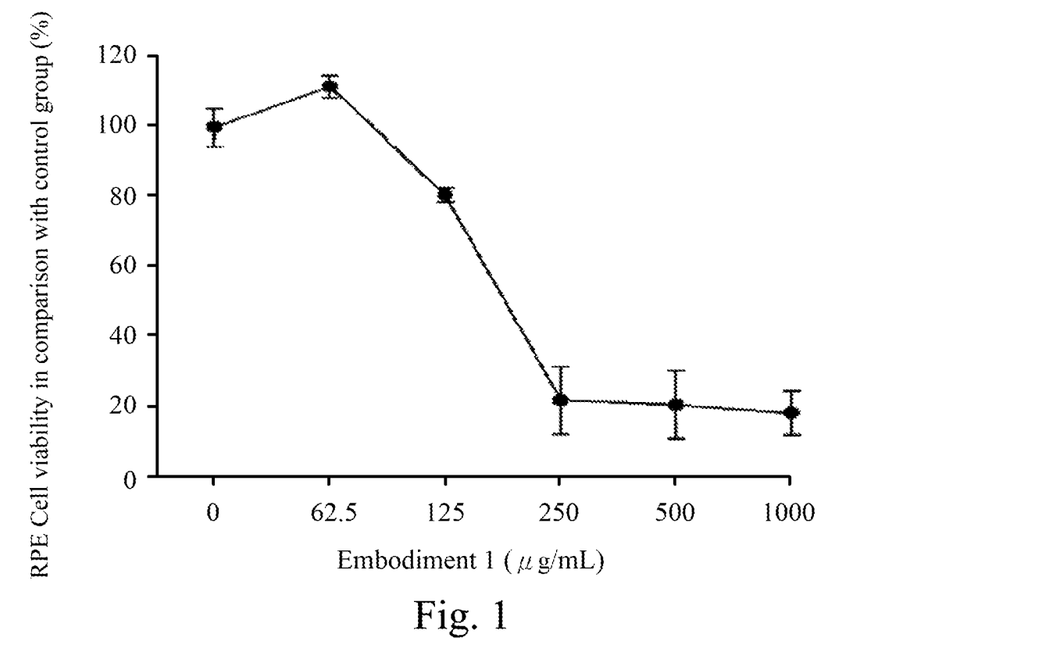
FIGS. 1-5 are diagrams showing cytotoxicity testing results according to the instant disclosure the instant disclosure.
Figure 2:
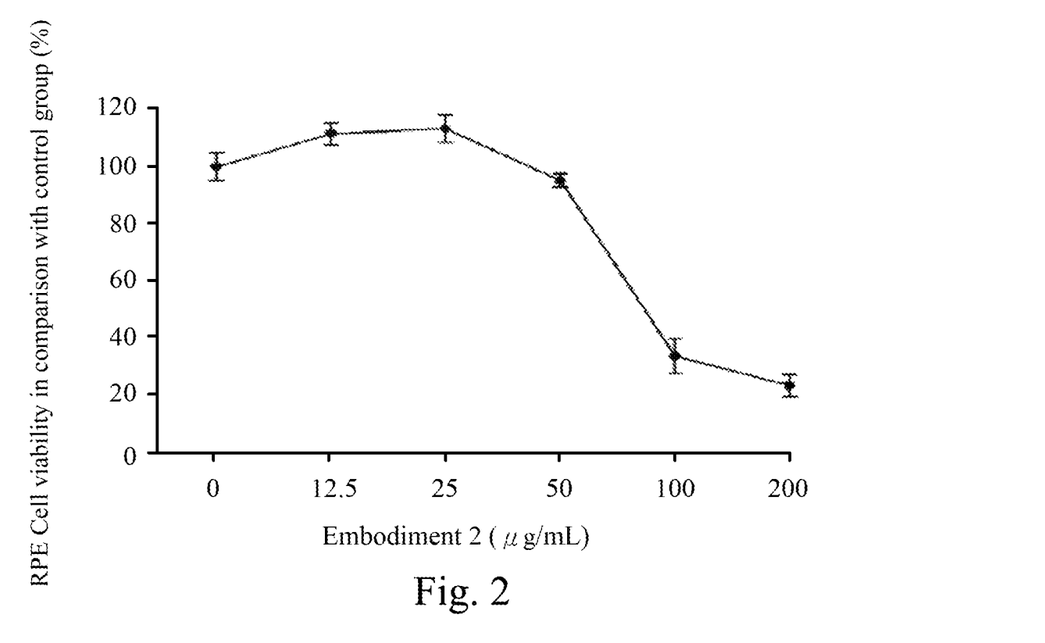
Figure 3:
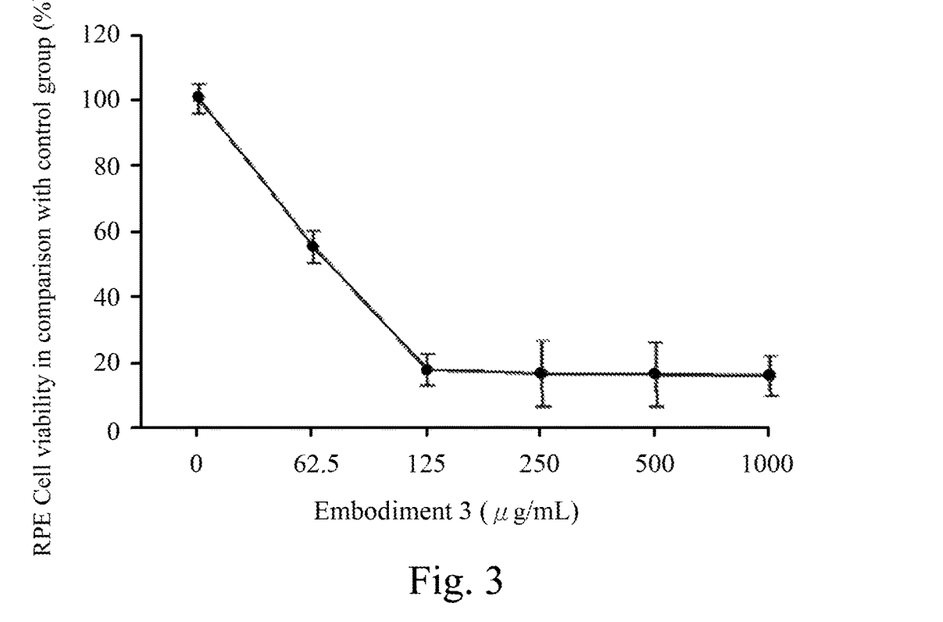
Figure 4:
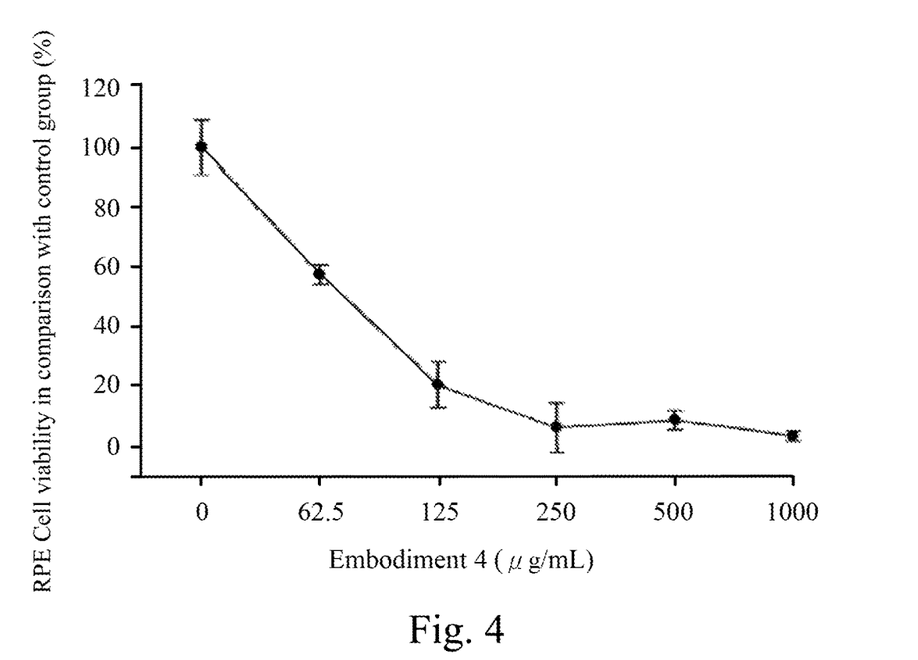
Figure 5:
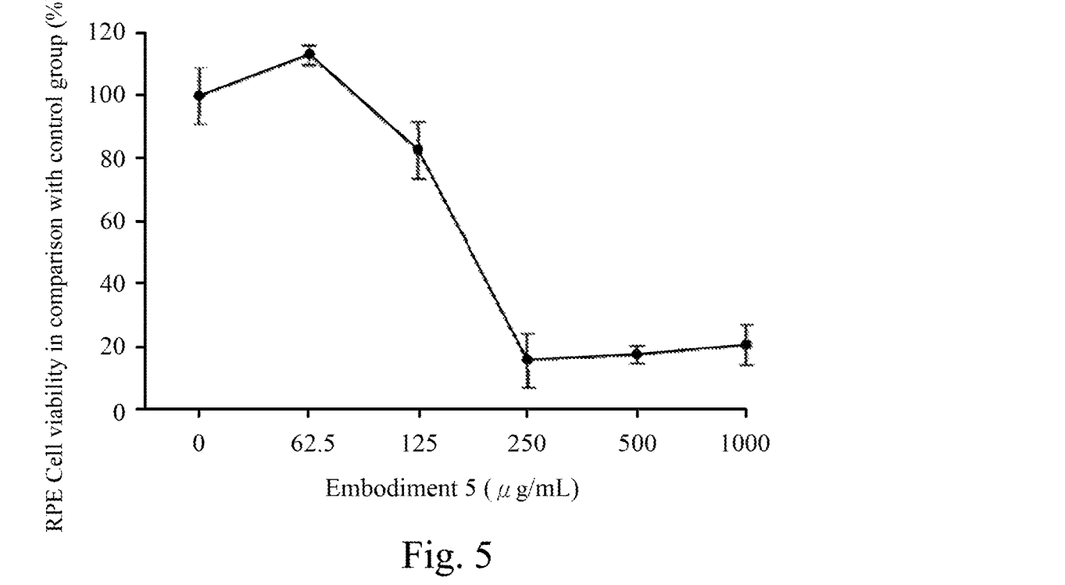

Referring to FIGS. 1-5, which are diagrams showing cytotoxicity testing results according to the instant disclosure respectively. From FIGS. 1-5, $IC_{25}$, $IC_{50}$ and $IC_{75}$ of embodiments 1-5 are listed, and the results are summarized in Table 1 below.

TABLE 1

| (µg/mL) | Embodiment 1 | Embodiment 2 | Embodiment 3 | Embodiment 4 | Embodiment 5 |
|---|---|---|---|---|---|
| $IC_{25}$ | 150 | 50 | 31.25 | 31.25 | 150 |
| $IC_{50}$ | 200 | 75 | 62.5 | 62.5 | 200 |
| $IC_{75}$ | 250 | 100 | 125 | 125 | 250 |

According to the results of Table 1, the $IC_{50}$ of embodiments 1-5 is sorted by values, which shows (embodiment 5, embodiment 1)>embodiment 2>(embodiment 3, embodiment 4). The testing concentration used in the subsequent example 2 was determined by the cytotoxicity test result of example 1.

Example 2: Effect of Embodiments 1-5 to Cell Viability and Growth of RPE Cells Treated by Reactive Oxygen Species (MTT Assay)

According to the cytotoxicity test result of example 1, three concentrations of embodiments 1-5 were used to test the damage of oxidative stress on the protective effect in example 2. The $IC_{50}$ of embodiments 1-5 were used as the highest concentrations in example 2 to reaffirm the action range of embodiments 1-5 to be toxic or to be a drug.

Before experiment, the medium was replaced by serum-free medium. Fixed quantity of RPE cells ($2 \times 10^5$ cells/mL) were respectively placed in 96 wells of a plate. After placed in an incubator, cells were treated by different concentrations of embodiments 1-5 and cultured for 24 hours. Next, different concentrations of oxidative stress inducer were added to treat the cells. The oxidative stress inducer used in example 2 includes hydrogen peroxide ($H_2O_2$, concentration 0.01-10 mM), tert-butyl hydroxyperoxide (t-BHP, concentration 0.01-10 mM), sodium azide ($NaN_3$, concentration 0.01-100 mM), and blue light-induced damage. The blue light having a wavelength of 480 nm and an illuminance of 350 lux was emitted by a blue light-emitting-diode (LED). Subsequently after treated by irradiating with blue light for 7 days or oxidative stress inducer for 24 hours, 0.5 mg/mL of MTT was added and reacted at 37° C. for 2 hours. Afterwards, 200 µL DMSO was added to each well. After slight mixing, the plate was vibrated in the dark for 10 minutes. After completely dissolving the residual cells, the enzyme immunoassay analyzer was used to detect the absorbance of each well. The cells untreated by oxidative stress inducers and embodiments were used as the control group. The cell viabilities relative to the control group was calculated by the cell viability calculating formula described in the example 1.

The results of the example 2 were expressed by the mean standard error of the number of experiments (mean±S.E.). The statistical analysis was performed by Student's t-test or one way ANOVA. If P<0.05, it indicates a significant difference.

The mechanisms of the oxidative stress inducer and RPE cell toxicants are summarized in Table 2 below.

TABLE 2

| Oxidative stress inducer | Toxicity Mechanism |
|---|---|
| $H_2O_2$ | 1. Free radical is a molecule having an unpaired electron, and the number thereof is an odd number. The free radical may be oxygen free radical, superoxide anion radical ($O_2^-$), hydroxyl radical ($OH^-$), and an intermediate, i.e. hydrogen peroxide ($H_2O_2$), for example. Generally, these free radicals are considered to be generated after local ischemia and reperfusion.<br>2. These active oxygen species are toxic to cells by attacking fatty acids to form peroxides of lipids and thus is toxic to the cells and react with proteins to damage and oxidize the amino acids, oxidize the sulfhydryl groups, and break the polypeptide chains. |
| t-BHP | 1. t-BHP is an organic hydroperoxide, and can be metabolized by glutathione peroxidase and oxidized glutathione (GSSG) in liver cells.<br>2. The exhaustion of glutathione (GSH) and the oxidation of NADPH is related to the constant of calcium ions and causes the cell viability being reduced.<br>3. In addition, t-BHP can be converted to peroxide or alkoxyl radicals by cytochrome P450 enzyme and free iron-dependent reaction.<br>4. Theses radicals may induce peroxidation of lipids and form covalent bonds with cellular molecules, such as DNAs and proteins, to further reduce the GSH content. In addition to affecting the constant of calcium ions, the effect of GSH also include the membrane potential of mitochondria to cause cell death. |
| $NaN_3$ | 1. $NaN_3$ is usually used to induce chemically induced mode of ischemia in cells and in vivo experiments. The exact mechanism is unclear.<br>2. The above effect is considered to be caused by $NaN_3$ inhibiting the cytochrome c oxidase (or known as respiratory chain complex IV) and blocks the electron transport chain to form peroxides. |
| Blue light | 1. Prolonged exposure to light may lead to age-related macular degeneration. The oxidative stress induced by light may be the key factor of RPE ceil degeneration.<br>2. Retina is protected from the UV injury by the cornea and crystalline lens absorbing UV having a wavelength below 400 nm, but retina may be damaged by visible light.<br>3. The blue region of spectrum (wavelength 400-500 nm) has relatively higher energy and may penetrate the tissue to the cells and the organelles. In particularly, it has been known that the blue light will damage the tissue of retina. |

Example 2 used embodiments 1-5 to respectively treat the RPE cells, and then used these oxidative stress inducers to treat the RPE cells. The protective effect of the embodiments 1-5 to the RPE cells was evaluated by the viability of the RPE cells.

Figure 6:
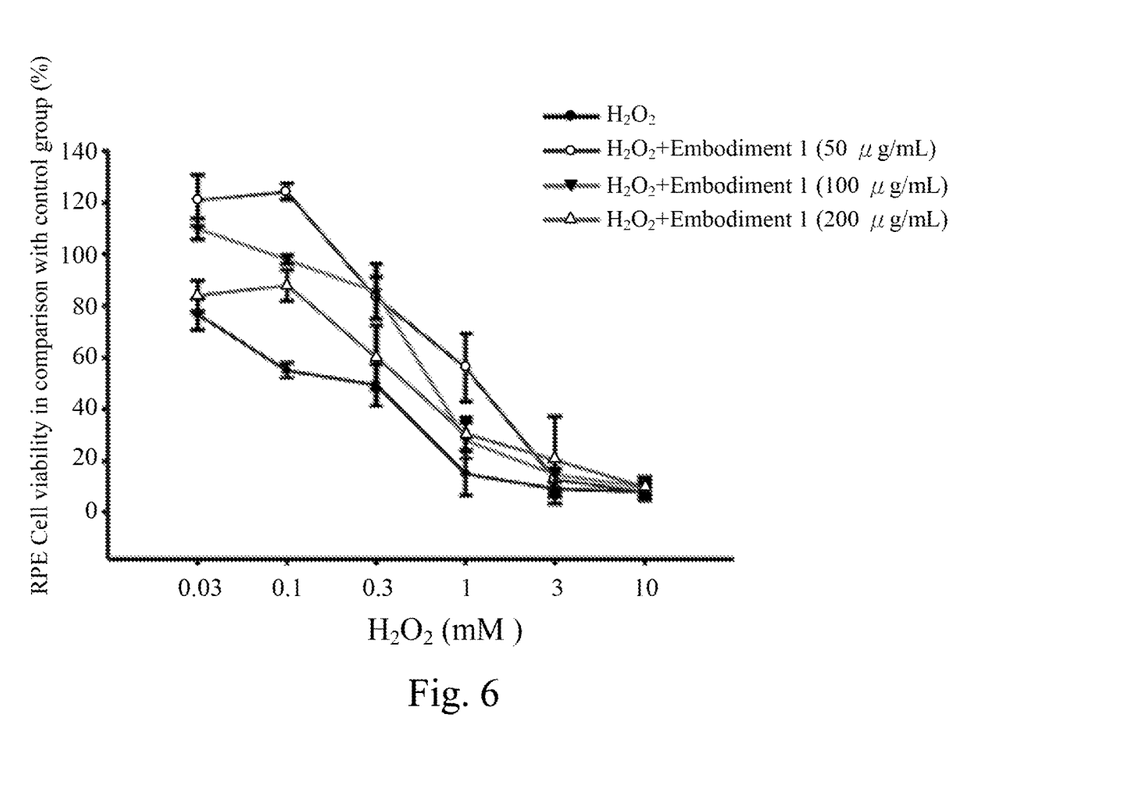
FIGS. 6-10 are diagrams showing testing results of protective effect of the embodiments in the instant disclosure to $H_2O_2$-induced cytotoxicity.
Figure 7:
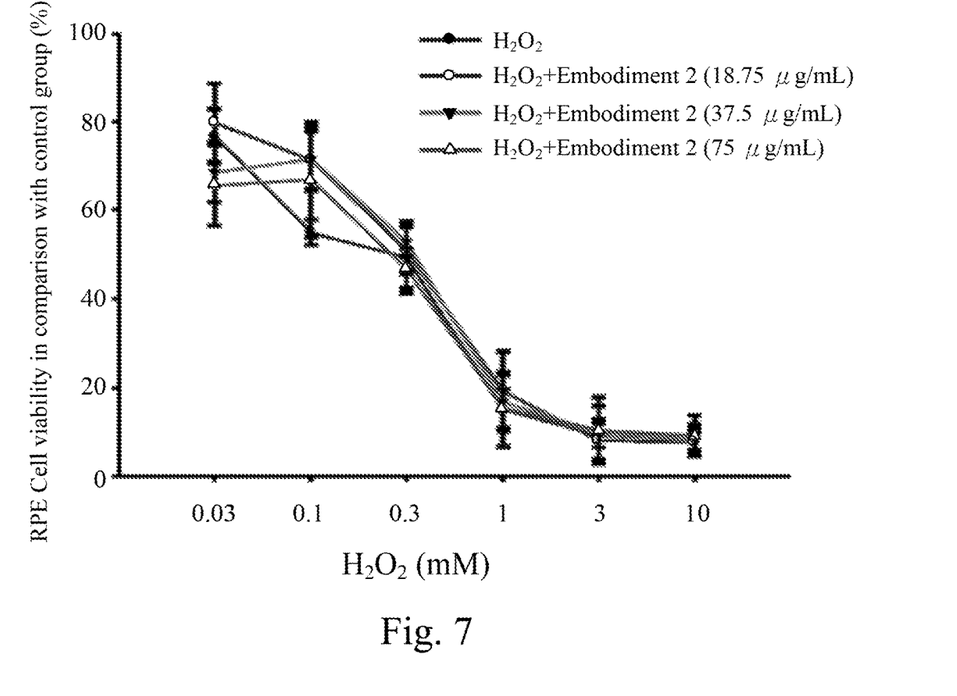
Figure 8:
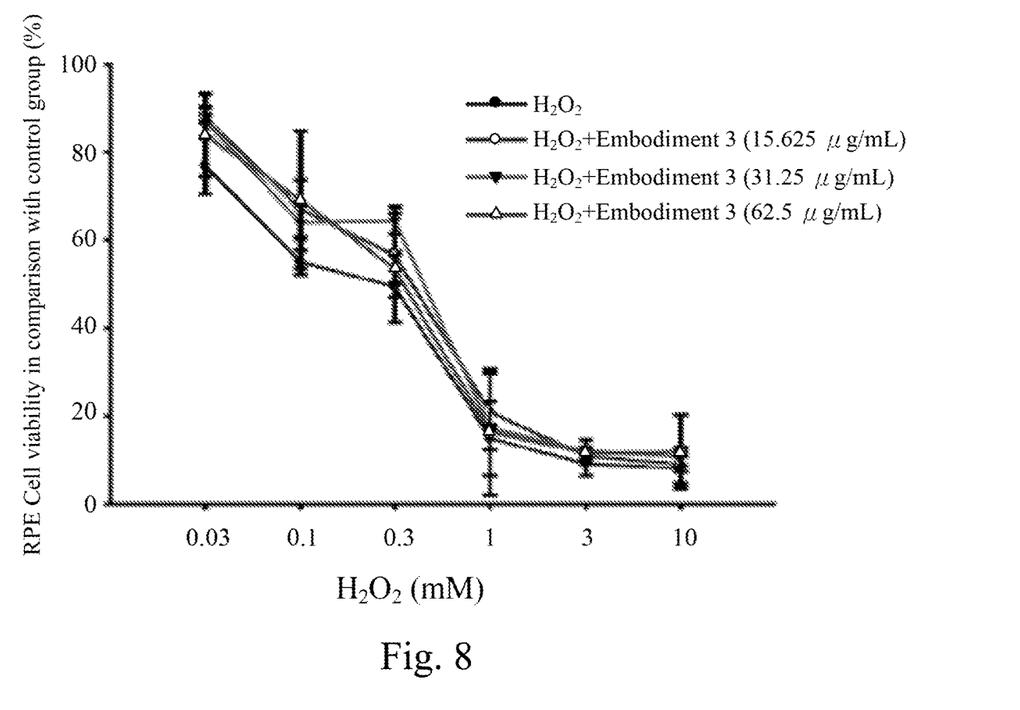
Figure 9:
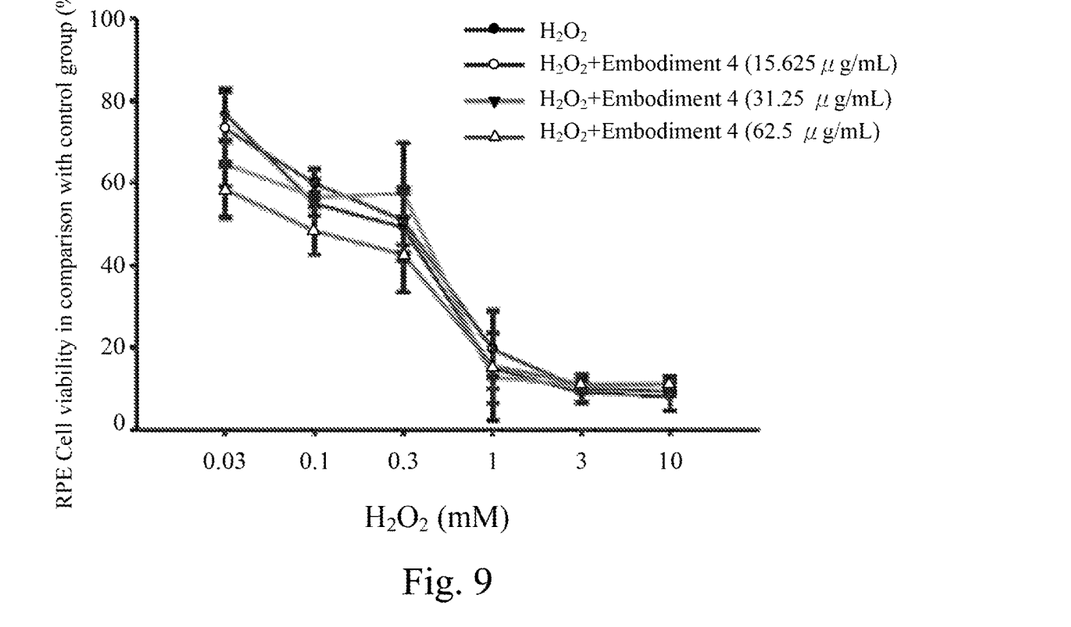
Figure 10:
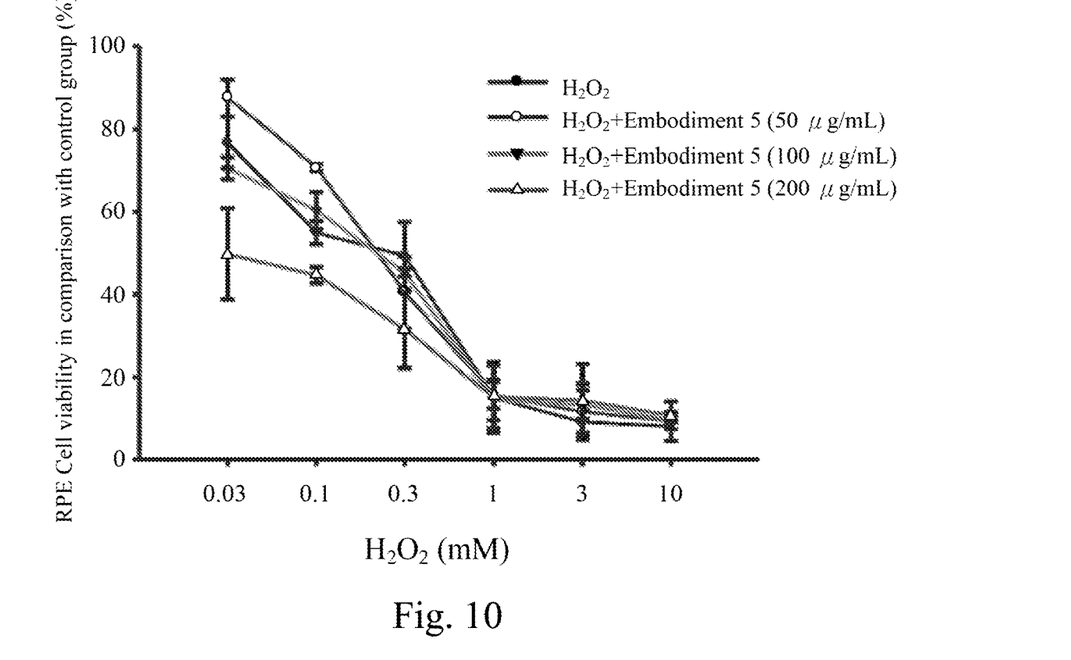

Referring to FIGS. 6-10, which are diagrams showing testing results of protective effect of embodiments 1-5 to $H_2O_2$-induced cytotoxicity. The concentrations of embodiment 1 were 50, 100, and 200 µg/mL. The concentrations of embodiment 2 were 18.75, 37.5, and 75 µg/mL. The concentrations of embodiment 3 were 15.625, 31.25, and 62.5 µg/mL. The concentrations of embodiment 4 were 15.625, 31.25, and 62.5 µg/mL. The concentrations of embodiment 5 were 50, 100, and 200 µg/mL. The testing results showed that 50% of RPE cells were dead after treated by 0.1 mM $H_2O_2$, i.e. the viability was about 50%. The cells may be protected by the embodiment 1, embodiment 2, embodiment 3, and embodiment 5 from the damage made at this concentration. Especially, the embodiment 1 had the strongest protection effect, and the cell viability was increased from 50% to 100% when the embodiment 1 was at concentrations of 50 µg/mL and 100 µg/mL. Moreover, when the concentration of the embodiment 1 was 200 µg/mL, reasonable cytotoxicity response was observed since the concentration was at the $IC_{50}$ concentration. The test results shown in FIGS. 6-10 also proved that the most effective action concentration range of the embodiment 1 to $H_2O_2$ was between 50 µg/mL and 100 µg/mL.

Figure 11:
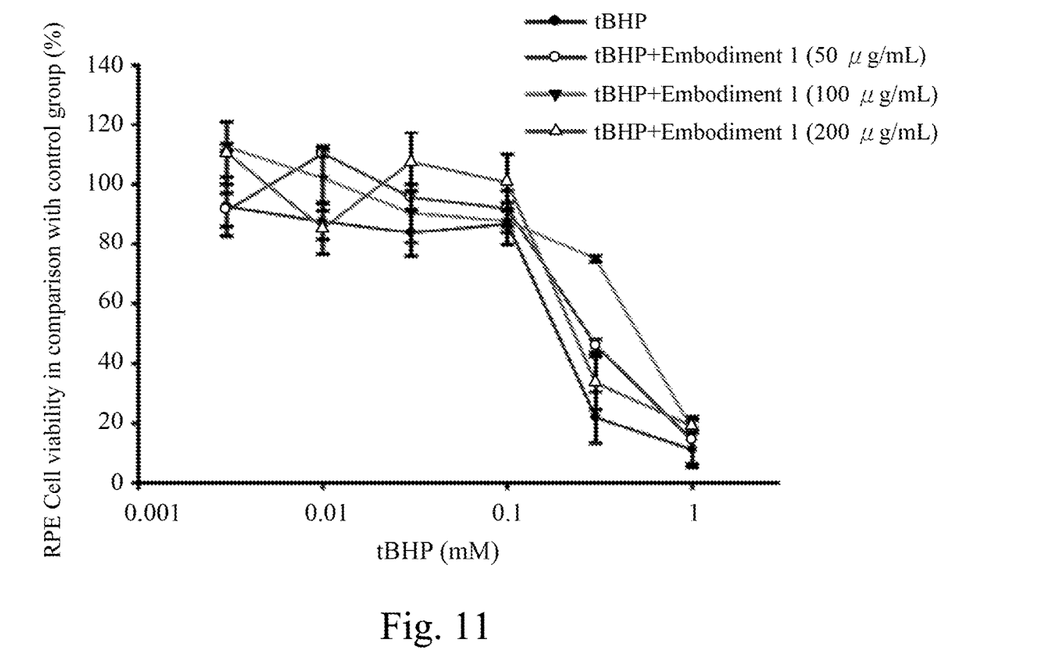
FIGS. 11-15 are diagrams showing testing results of protective effect of the embodiments in the instant disclosure to t-BHP-induced cytotoxicity.
Figure 12:
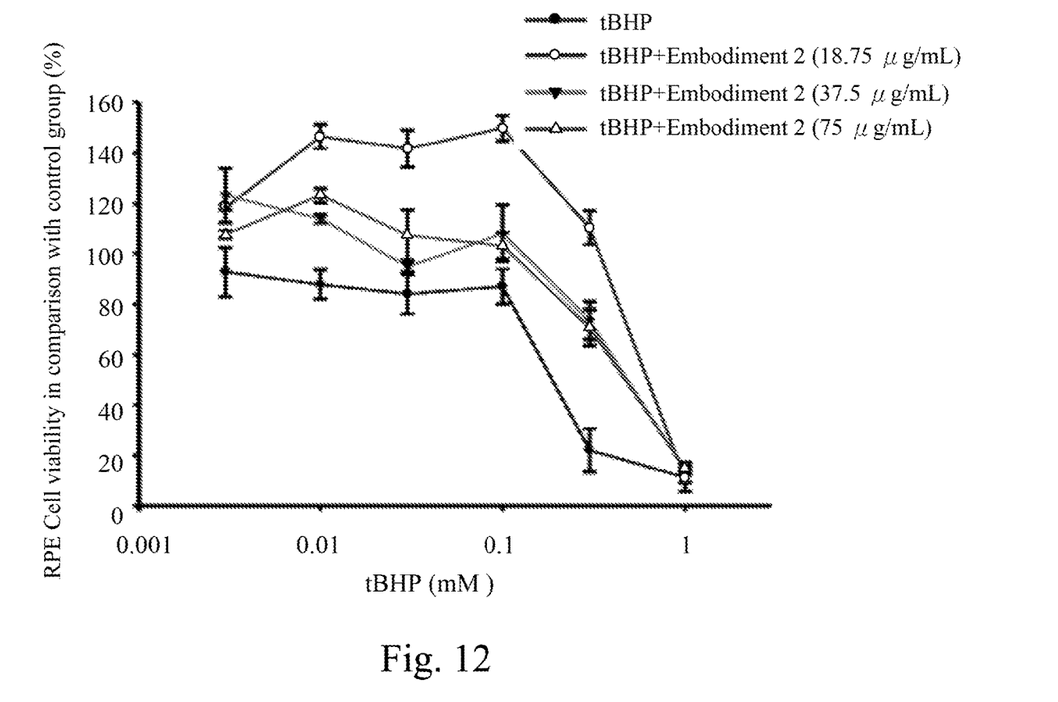
Figure 13:
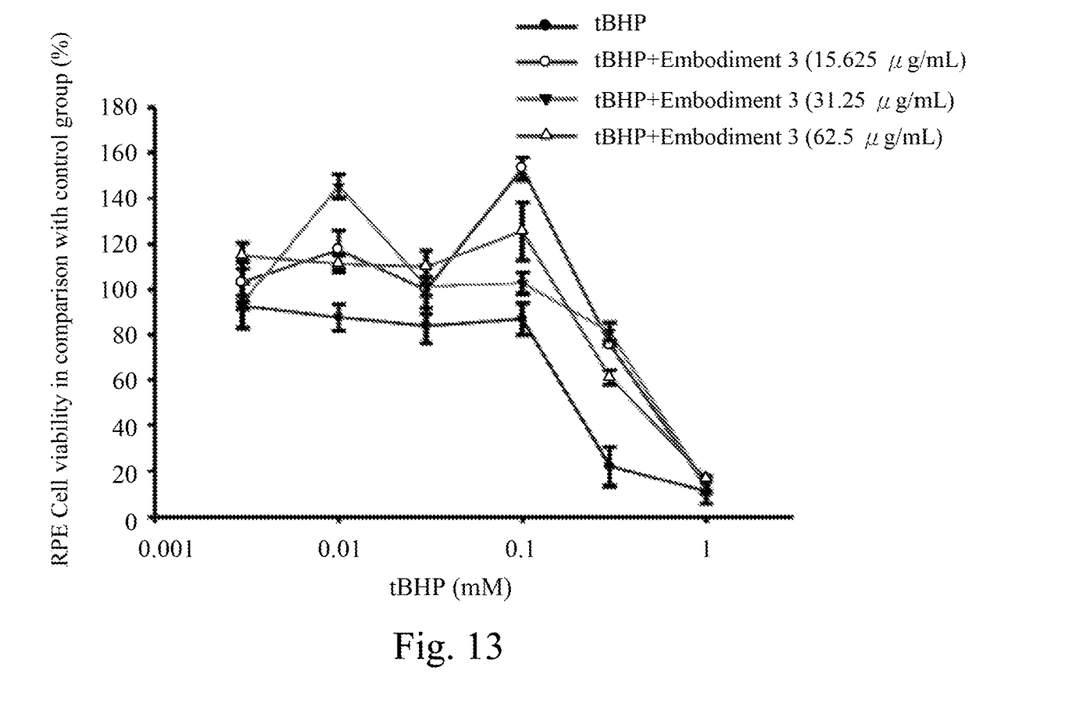
Figure 14:
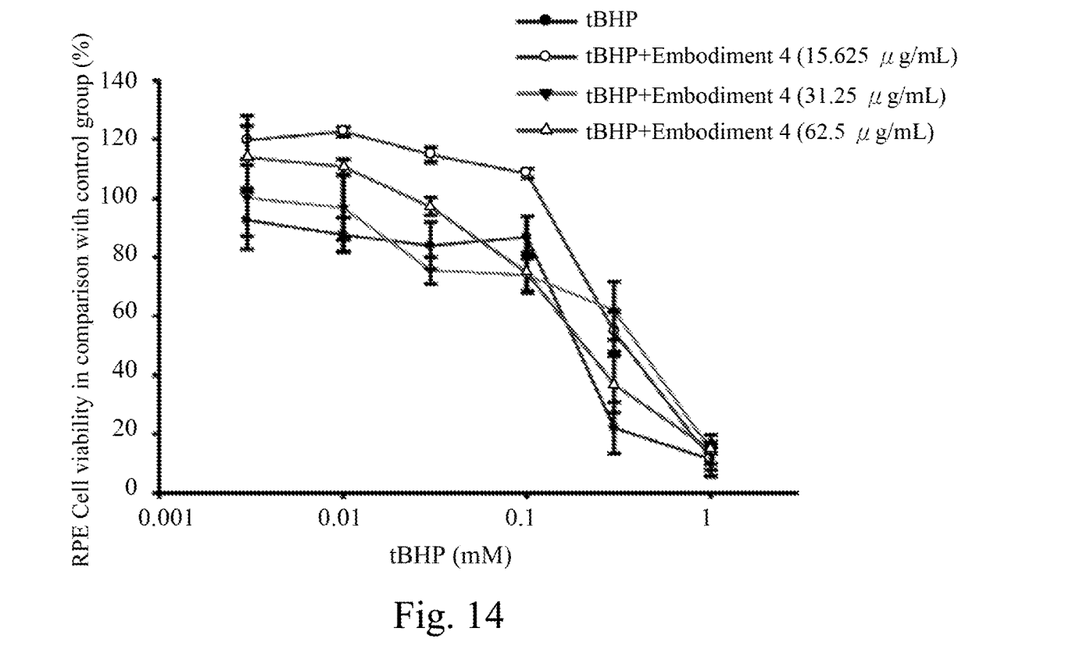
Figure 15:
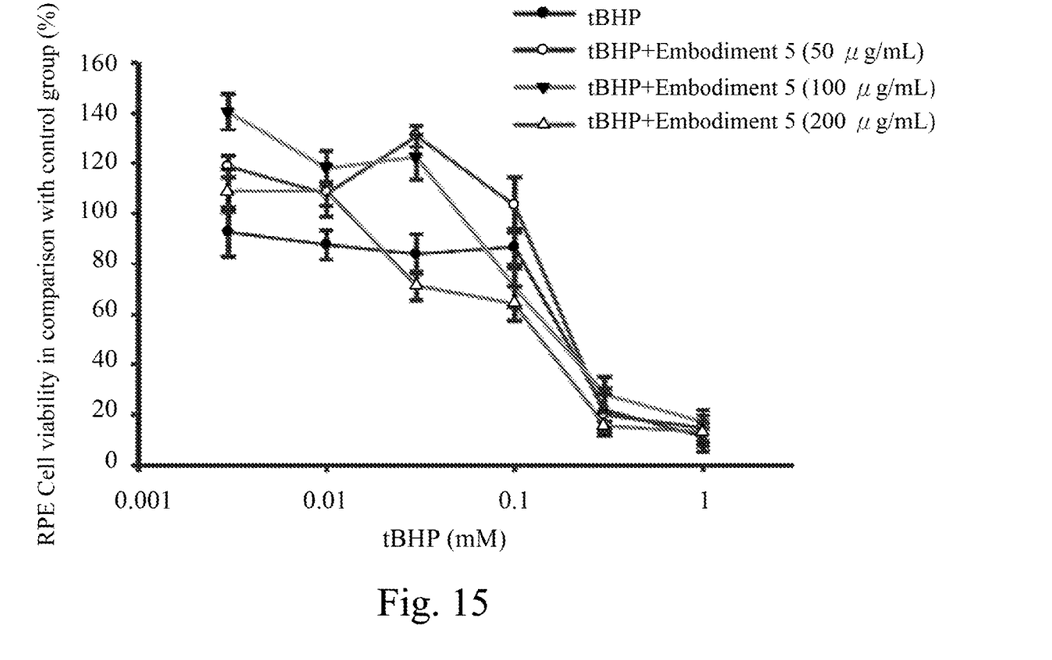

Referring to FIGS. 11-15, which are diagrams showing testing results of protective effect of the embodiments 1-5 to t-BHP-induced cytotoxicity. The concentrations of embodiment 1 were 50, 100, and 200 µg/mL. The concentrations of embodiment 2 were 18.75, 37.5, and 75 µg/mL. The concentrations of embodiment 3 were 15.625, 31.25, and 62.5 µg/mL. The concentrations of embodiment 4 were 15.625, 31.25, and 62.5 µg/mL. The concentrations of embodiment 5 were 50, 100, and 200 µg/mL. The testing results showed that 80% of RPE cells were dead after treated by 0.3 mM t-BHP, i.e. the viability was about 20%. The cells may be protected by all of the embodiments 1-5 from the damage made at this concentration. Especially, the embodiments 1, 2, and 3 had the strongest protection effect, and the cell viability was increased from 20% to above 80% when the embodiments 1 2, and 3 were at low and medium concentrations. Moreover, when embodiments 1 2, and 3 were at high concentrations, reasonable cytotoxicity responses were observed since the high concentrations were at the $IC_{50}$ concentrations. The test results shown in FIGS. 11-15 also proved that the most effective action concentration ranges of the embodiments 1, 2, and 3 to t-BHP was between low and medium concentrations.

Figure 16:
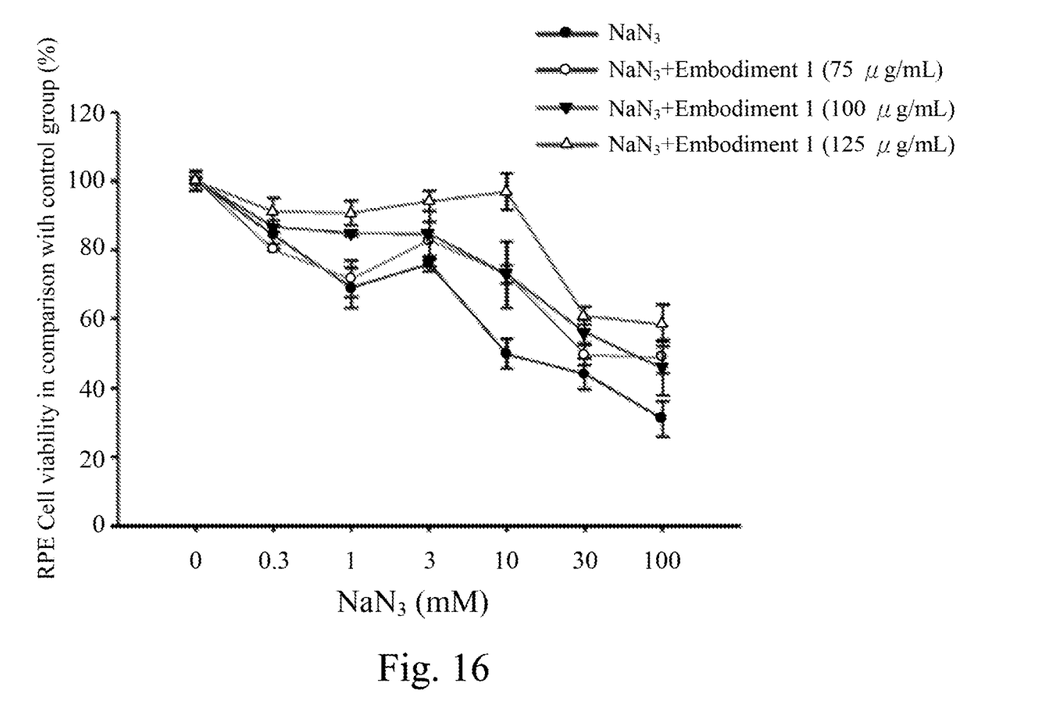
FIGS. 16-20 are diagrams showing testing results of protective effect of the embodiments in the instant disclosure to $NaN_3$-induced cytotoxicity.
Figure 17:
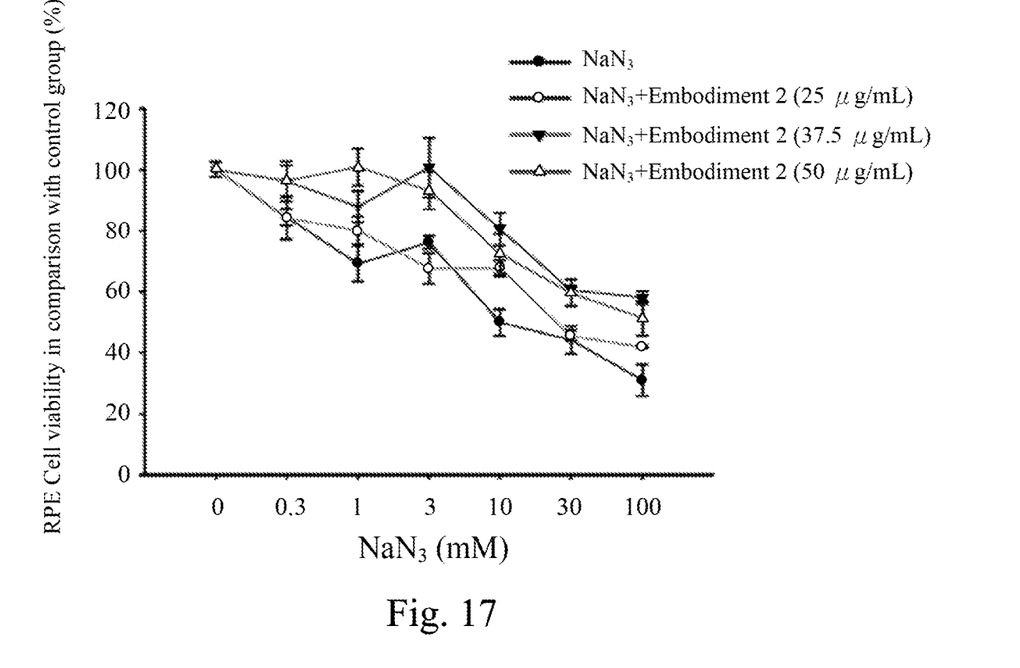
Figure 18:
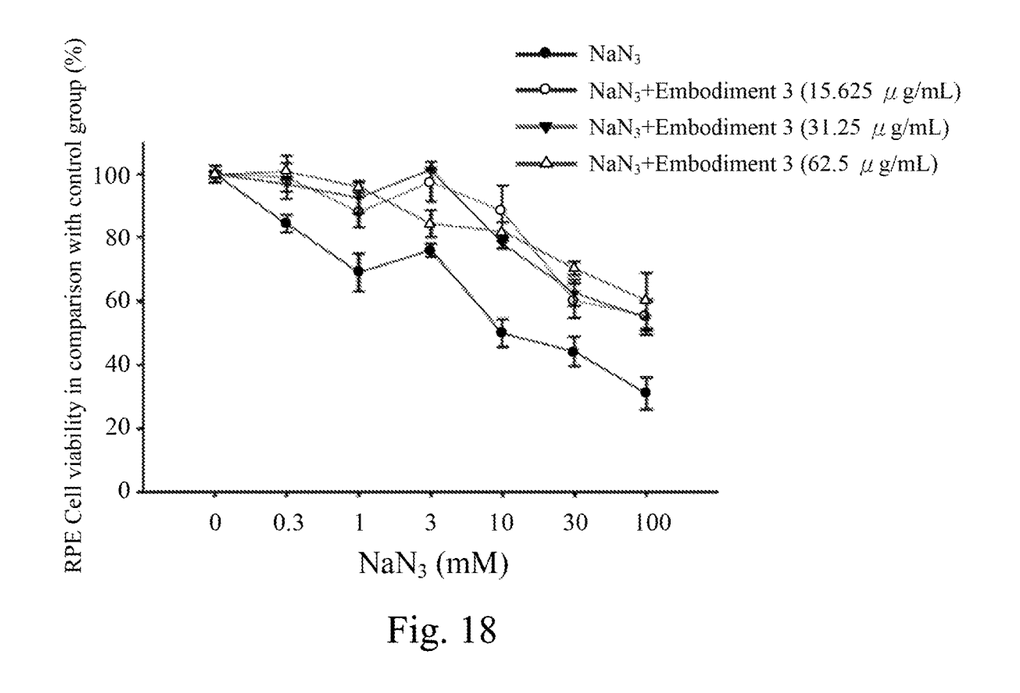
Figure 19:
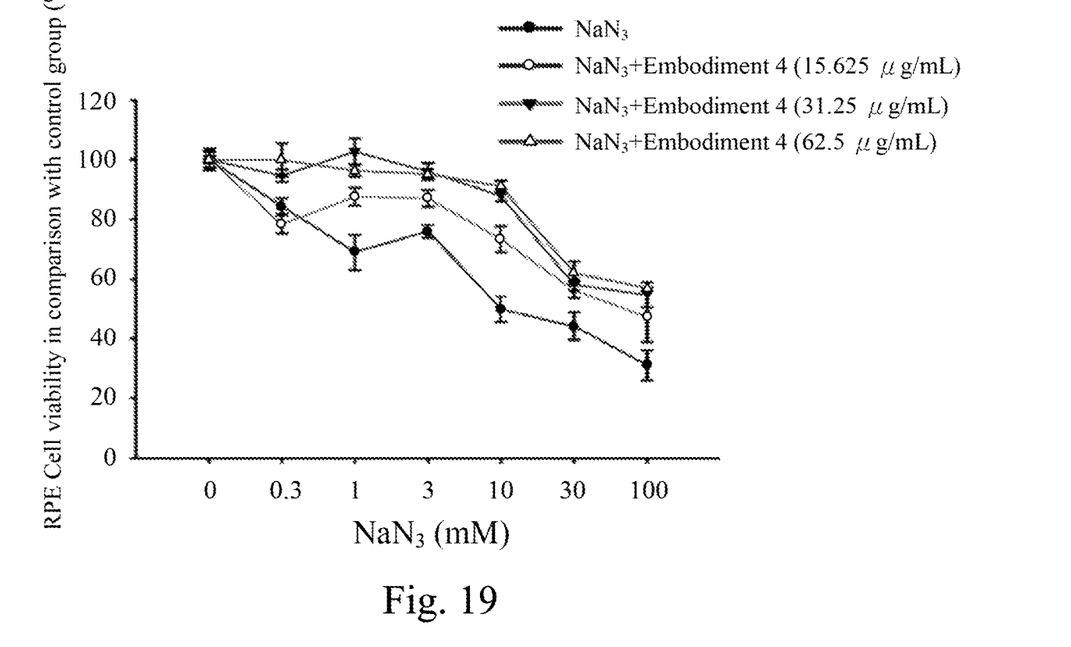
Figure 20:
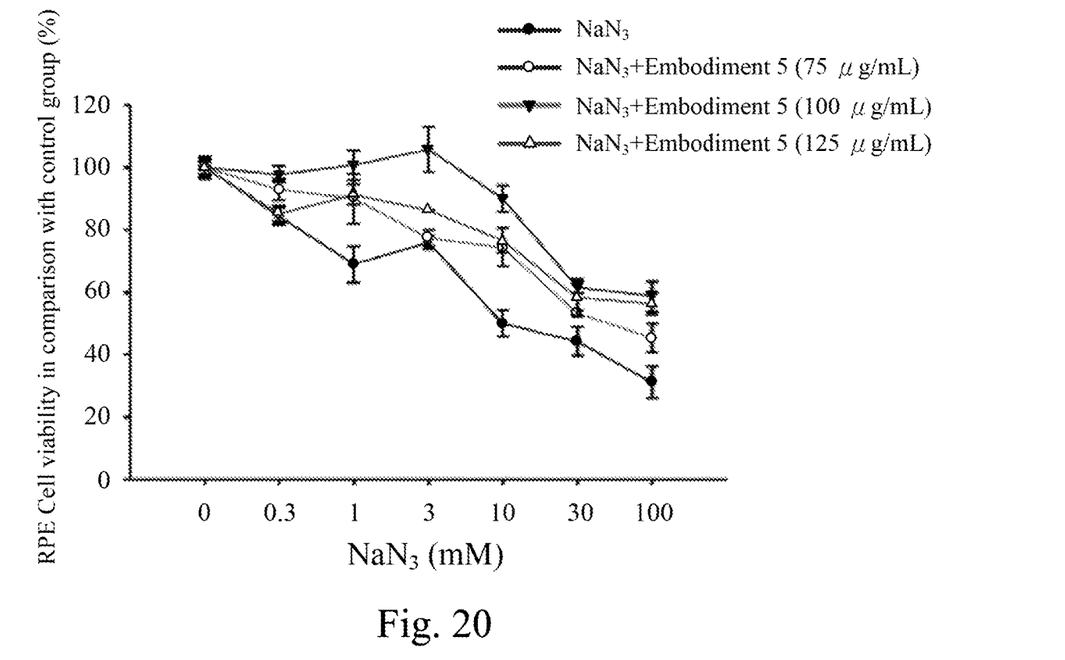

Referring to FIGS. 16-20, which are diagrams showing testing results of protective effect of the embodiments 1-5 to $NaN_3$-induced cytotoxicity. The concentrations of embodiment 1 were 75, 100, and 125 µg/mL. The concentrations of embodiment 2 were 25, 37.5, and 50 μg/mL. The concentrations of embodiment 3 were 15.625, 31.25, and 62.5 μg/mL. The concentrations of embodiment 4 were 15.625, 31.25, and 62.5 μg/mL. The concentrations of embodiment 5 were 75, 100, and 125 μg/mL. The testing results showed that 50% of RPE cells were dead after treated by 10 mM $NaN_3$, i.e. the viability was about 50%. The cells may be protected by all of the embodiments 1-5 from the damage made at this concentration. Especially, the embodiments 1, 4, and 5 had the strongest protection effect, and the cell viability was increased to almost 100% when the embodiments 1, 4, and 5 were at medium and high concentrations. The embodiments 2 and 3 come next. The cell viability was increased from 50% to above 80%. Moreover, the high concentrations of the embodiments 1-5 under the damage of $NaN_3$ did not show serious toxicity. This result showed that the $IC_{50}$ might fall into the range of the drug effect but did not show dose-dependent relationship. The test results shown in FIGS. 16-20 proved that the most effective action concentration range of the embodiments 1-5 to $NaN_3$ was between low and medium concentrations.

Figure 21:
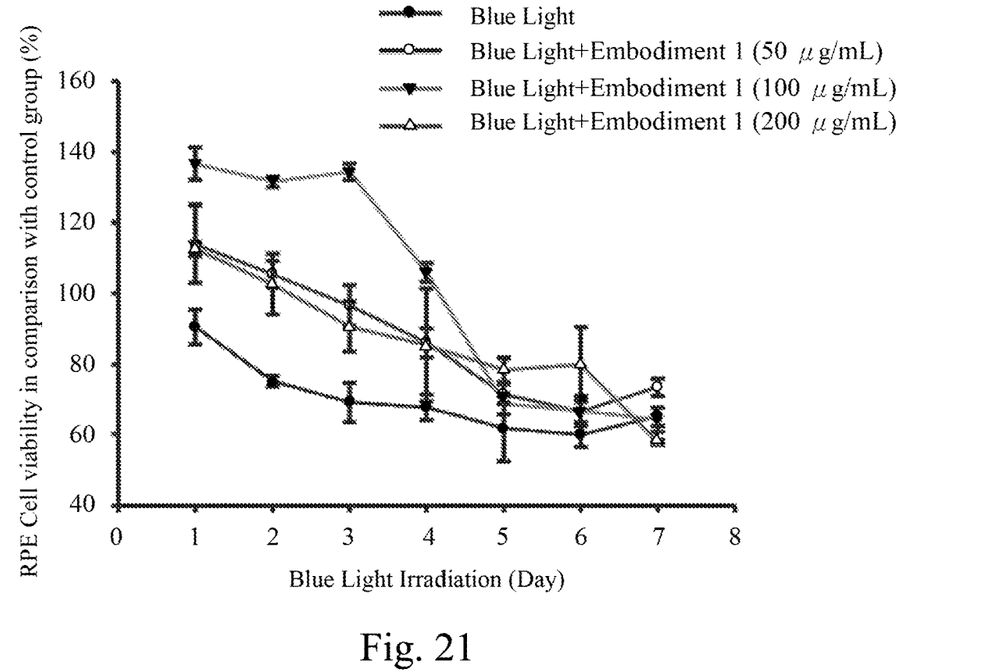
FIGS. 21-25 are diagrams showing testing results of protective effect of the embodiments in the instant disclosure to blue light-induced cytotoxicity.
Figure 22:
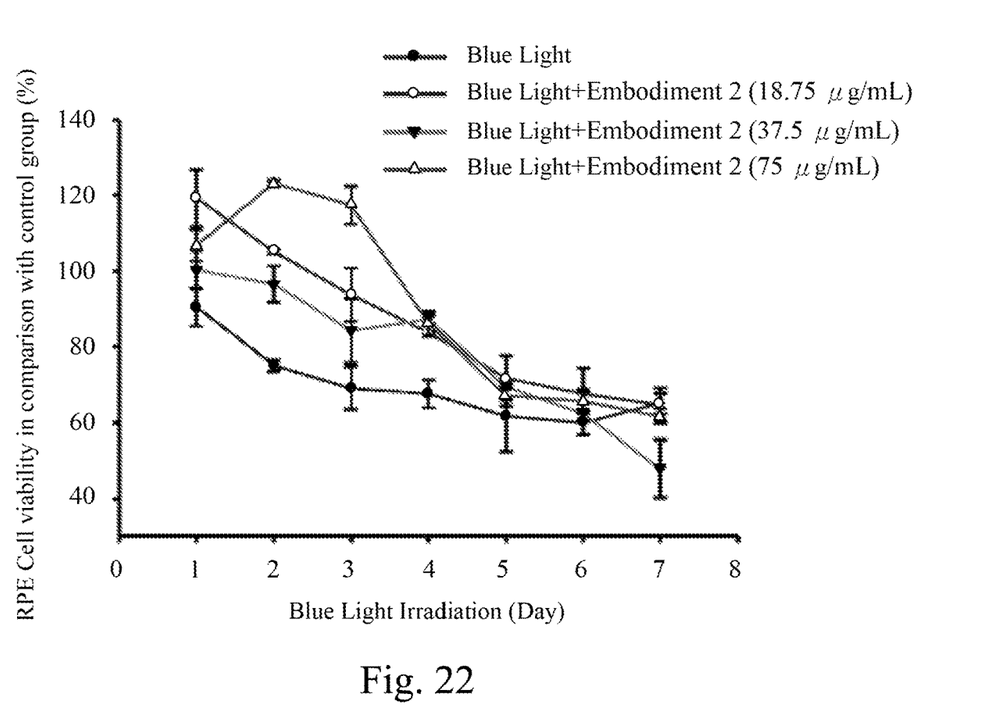
Figure 23:
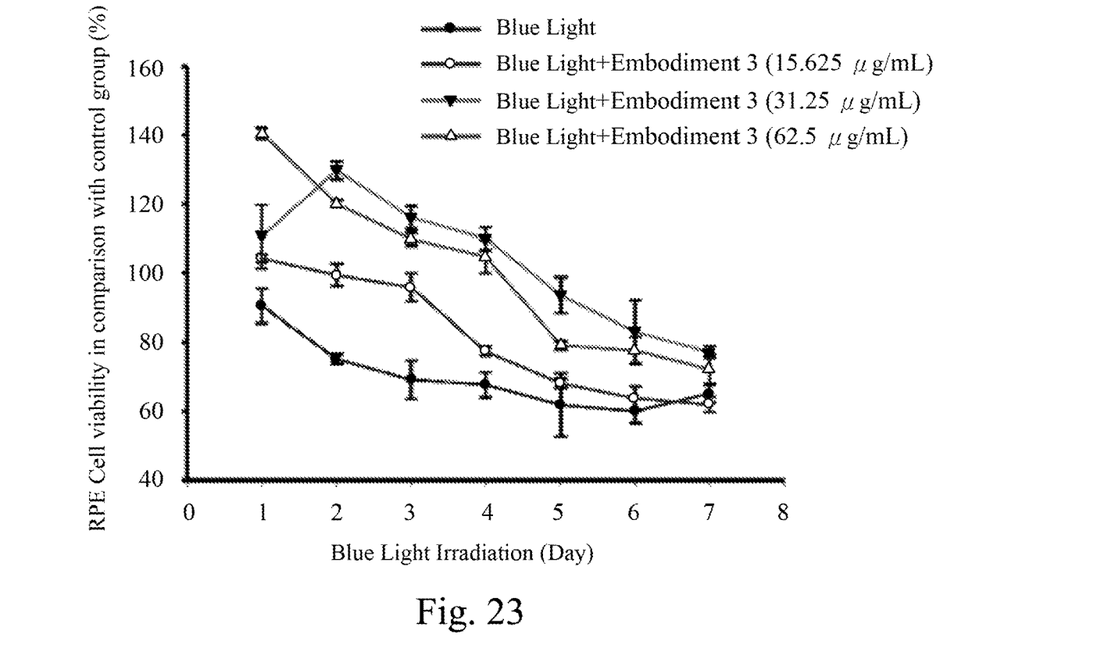
Figure 24:
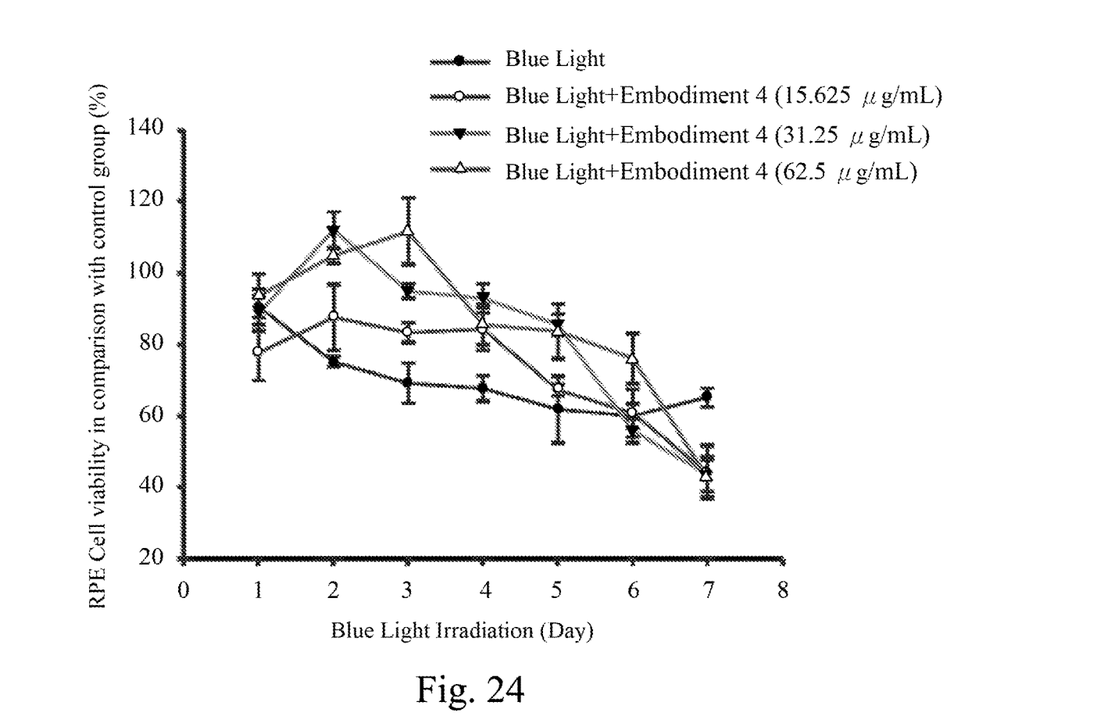
Figure 25:
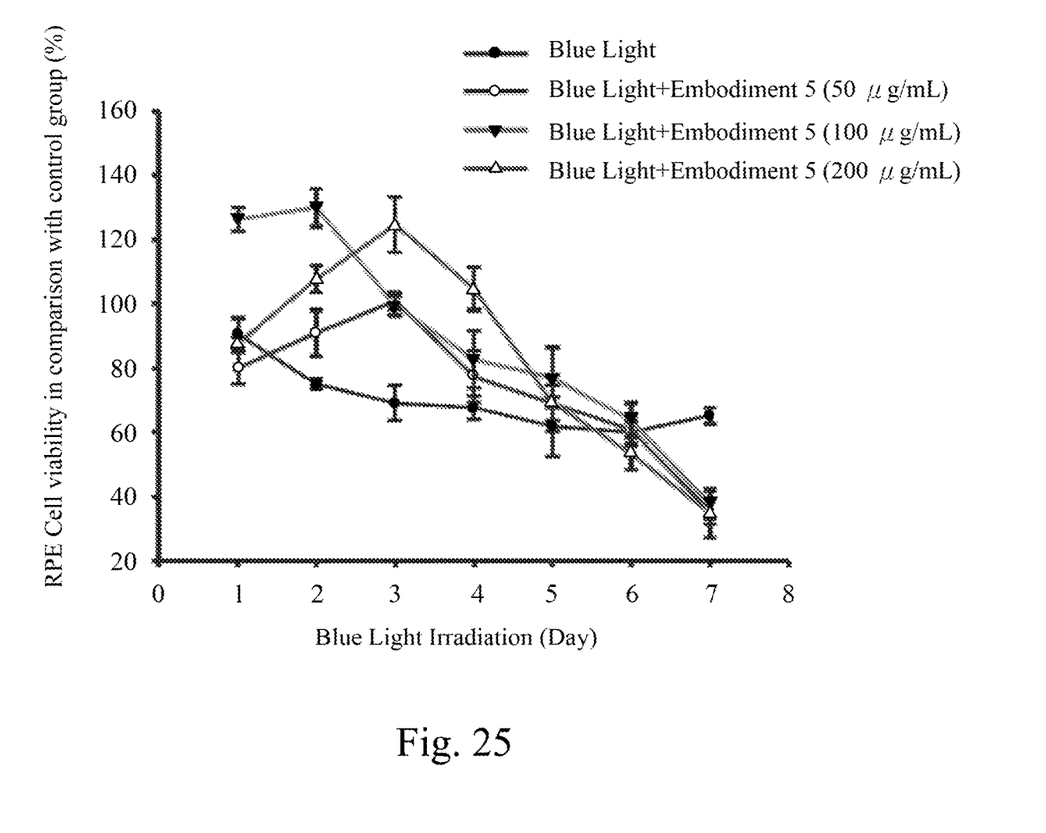

Referring to FIGS. 21-25, which are diagrams showing testing results of protective effect of the embodiments 1-5 to blue light irradiation-induced cytotoxicity. The concentrations of embodiment 1 were 50, 100, and 200 μg/mL. The concentrations of embodiment 2 were 18.75, 37.5, and 75 μg/mL. The concentrations of embodiment 3 were 15.625, 31.25, and 62.5 μg/mL. The concentrations of embodiment 4 were 15.625, 31.25, and 62.5 μg/mL. The concentrations of embodiment 5 were 50, 100, and 200 μg/mL. The test results showed that 40% RPE cells were dead after treated by irradiating with blue light (480 nm, 30 lux) for 5 days, i.e. the viability was about 60%. The cells may be protected by all of the embodiments 1-5 from the damage made at this concentration. Especially, the embodiments 3 and 4 had the strongest protection effect, and the cell viability was increased from 60% to above 90%-100% when the embodiments 3 and 4 were at medium concentrations. Moreover, when embodiments 1-5 were at high concentrations, reasonable cytotoxicity responses were observed since the high concentrations were at the $IC_{50}$ concentrations. The test results shown in FIGS. 21-25 also proved that the most effective action concentration ranges of the embodiments 3 and 4 to blue light irradiation was between low and medium concentrations.

Analyzing the test results of examples 1 and 2 in the instant disclosure, it was found that in the process of embodiments 1-5 antagonizing the damage caused by oxidative stress inducer, the embodiments 1-5 can react with oxidative stress inducer to change the structure and cause property change. The property of the embodiments 1-5 was converted from reductant to oxidant. The property of the oxidative stress inducer was converted from oxidant to reductant. Therefore, the effect of the embodiments 1-5 against the oxidative stress inducer and the damage of the oxidative stress inducer to the cells both decreased. This situation would become more obvious when the concentrations of the embodiments 1-5 and the oxidative stress inducer were increased.

The test results of the all oxidative stress inducers in the example 2 were summarized in Table 3 below.

TABLE 3

The protective effects of the embodiments 1-5 on the induced damage to the RPE cells caused by oxidative stress inducer

|  | $H_2O_2$ | t-BHP | $NaN_3$ | Blue light |
|---|---|---|---|---|
| Embodiment 1 | ✓✓ | ✓ | ✓✓ | ✓ |
| Embodiment 2 | ✓ | ✓✓ | ✓ | ✓ |
| Embodiment 3 | ✓ | ✓ | ✓ | ✓✓ |
| Embodiment 4 | x | ✓ | ✓✓ | ✓✓ |
| Embodiment 5 | ✓ | ✓ | ✓✓ | ✓ |

"✓✓" represents excellent protective action;
"✓" represents good protective action; and
"x" represents no obvious protective action.

From the summary of Table 3, it can be found that the embodiments 1-5 had protective effect on the damage caused by t-BHP, $NaN_3$ and blue light to the RPE cells, wherein the embodiments 1 and 4 had even stronger protective effect.

In summary, the instant disclosure provides a method of using extract of *Cistanche tubulosa* for preparing drugs or food to protect eye cells. The extract of *Cistanche tubulosa* can decrease the damage of the oxidative stress to the eye cells. Therefore, the drugs and food prepared from the extract of *Cistanche tubulosa* have good protective effect to the eye cells and can be further developed to the drugs and food of preventing eye diseases or slow downing the progress of eye disease.

Although the embodiments of the present invention have been disclosed as above, it is not intended to limit the present invention. Any person skilled in the art can make various modifications and variations without departing from the spirit and scope of the present invention. Therefore, the scope of the invention should be as defined by the appended claims.

What is claimed is:

1. A method of treating an eye disease caused by oxidative stress from blue light irradiation comprising: administrating to a subject in need thereof a therapeutically effective amount of an aqueous extract of *Cistanche tubulosa*, wherein the extract contains echinacocide, aceteoside, isoacteoside, and tubuloside A, and wherein the eye disease is macular degeneration and/or retinopathy.

2. The method of claim 1, wherein the macular degeneration is age-related macular degeneration.

3. The method of claim 2, wherein the age-related macular degeneration is dry macular degeneration or wet macular degeneration.

4. The method of claim 1, wherein the retinopathy is diabetic retinopathy, retinitis pigmentosa, retina disease, retinal artery and vein occlusion, proliferative vitreoretinopathy, or central serous retinopathy.

* * * * *